(12) United States Patent
Graydon

(10) Patent No.: US 9,192,686 B2
(45) Date of Patent: Nov. 24, 2015

(54) APPARATUS FOR DRYING AND SANITIZING HANDS

(76) Inventor: Brian Graydon, Dublin (IE)

( * ) Notice: Subject to any disclaimer, the term of this patent is extended or adjusted under 35 U.S.C. 154(b) by 0 days.

(21) Appl. No.: 13/992,702

(22) PCT Filed: Dec. 6, 2011

(86) PCT No.: PCT/EP2011/071905
§ 371 (c)(1),
(2), (4) Date: Oct. 8, 2014

(87) PCT Pub. No.: WO2012/076521
PCT Pub. Date: Jun. 14, 2012

(65) Prior Publication Data
US 2015/0048160 A1  Feb. 19, 2015

(30) Foreign Application Priority Data
Dec. 7, 2010 (IE) .................... S2010/0768

(51) Int. Cl.
*A61L 2/18* (2006.01)
*A47K 10/48* (2006.01)
*G07C 9/00* (2006.01)

(52) U.S. Cl.
CPC . *A61L 2/18* (2013.01); *A47K 10/48* (2013.01); *G07C 9/00111* (2013.01)

(58) Field of Classification Search
CPC ....... A61L 2/18; A47K 10/48; G07C 9/00111
USPC .................................. 235/380, 492
See application file for complete search history.

(56) References Cited

U.S. PATENT DOCUMENTS

2009/0267776 A1* 10/2009 Glenn et al. ............... 340/573.1
2010/0155420 A1* 6/2010 Glenn et al. .................... 222/88

FOREIGN PATENT DOCUMENTS

DE            10146290 A1 * 4/2003

* cited by examiner

*Primary Examiner* — Kristy A Haupt
(74) *Attorney, Agent, or Firm* — Thomas M. Freiburger

(57) ABSTRACT

An apparatus for sanitizing hands (400) comprising a housing (402) having a hand placement area (403) and a hand sanitizing means (420, 421, 406) to in use spray a hand sanitizing fluid into the placement area (403), and means (414) to provide an airflow to dry hands in the placement area.

23 Claims, 5 Drawing Sheets

APPARATUS FOR DRYING AND SANITIZING HANDS

BACKGROUND OF THE INVENTION

This application claims priority from Irish patent application number S2010/0768, filed Dec. 7, 2010, and PCT/EP2011/071905, filed Dec. 6, 2011.

Hot air hand drying apparatus for public restrooms are well known and operate by blowing hot air unto a user's wet hands to as to facilitate drying of the hands. There are a number of disadvantages associated with these apparatus. Firstly, they can be unreliable and often operate to sub-optimal levels. For example, the heating element may fail resulting in cold air being blown onto a user's hands, which is ineffectual at drying. In some cases, the flow of air is very weak either due to poor design or part failure, again ineffectual for drying. This may lead to a person leaving the bathroom with hands still damp, which may encourage bacterial growth from the moisture left on their hands.

A further advantage associated with hot air blowing hand driers is that they can harbour micro-organisms, including airborne pathogens, such that a person's hands may be less clean after using the drier than before, which is obviously counter-productive.

The blowing action of these devices also results in the distribution of the airborne micro-organisms throughout the room in which the apparatus in located, greatly compromising the hygiene of that area. Additionally, these devices can also be quite energy inefficient.

Furthermore, many people don't adhere to best practice by washing their hands properly, and to add to that many people don't bother to wash their hands at all, as it is perceived to be a lengthy and cumbersome operation. This means many washrooms and their users are potentially left in an unhygienic state.

It is an object therefore of the present invention to provide an apparatus for drying hands that overcomes at least some of the above-mentioned problems.

STATEMENTS OF INVENTION

According to the invention there is provided an apparatus for drying hands, the apparatus comprising a hand placement area and means for generating a substantially circulating airflow along an airflow path, such that the hand placement area is located in the airflow path.

In this way, the circulating air-flow reduces the effect of the airflow on the air in the surrounding area and thus reduces the distribution of any airborne micro-organisms in or near the device into the surrounding area. Furthermore the device applies two drying forces to the user's hand in the hand placement area—a blowing force caused by the air on the outward part of the circulating airflow and a suction force caused by the air on the return part of the circulating airflow. This increases the efficiency of the drying process, thus using less energy.

In one embodiment of the invention there is provided an apparatus for drying hands in which the hand placement area is partially enclosed and has a hand placement aperture. In this way, the circulating air flow will also be partially enclosed, which will assist in maintaining the circulating airflow in the hand placement area. Additionally, the user will be able to access the circulating airflow through the hand placement aperture.

In another embodiment of the invention there is provided an apparatus for drying hands in which the hand placement area comprises an airflow inlet and an airflow outlet. In this way, the circulating airflow can be maintained in the hand placement area.

In a further embodiment of the invention there is provided an apparatus for drying hands in which the means for generating an airflow comprises an airflow generator connected between the airflow inlet and an airflow outlet. In this way, the circulating airflow may be generated.

In an alternative embodiment of the invention there is provided an apparatus for drying hands in which the airflow generator is adapted to cause an air inflow at the airflow inlet and an air outflow at the airflow outlet. In this way, the circulating airflow may be maintained in the hand placement area.

The invention further provides an apparatus as claimed in Claim 1. In this way, the user's hands may be sanitized while using the device. This preferred embodiment would reduce the requirement for water while cleaning hands. A user would simply place dry dirty hands into the hand placement area, and his hands are sanitized and then dried.

Preferably there is provided a plurality of nozzles.

Further preferably there is provided a reservoir for hand sanitizing fluid.

Preferably there is further provided a tank of concentrated sanitizer liquid connected to the reservoir for sanitizer fluid.

The reservoir for hand sanitizing fluid is preferably connected to a water supply.

Preferably there is provided an atomizer pump connected between the reservoir and the nozzles.

The tank preferably is connected to the reservoir via a dosing pump (430).

The water supply is preferably controlled via a ball cock.

The reservoir preferably comprises a sensor means to control the water supply to the reservoir and to control the dosing pump to supply concentrated sanitizer liquid to the reservoir.

The dosing pump in use preferably injects concentrated sanitizer liquid into the reservoir and water is supplied to the reservoir to achieve the preferred necessary concentration of sanitizer liquid.

Preferably the apparatus comprises a sensor to detect an identification tag on a user, to record usage of the apparatus by the user.

Preferably there is provided means to activate the apparatus, in response to detection of a tag worn by a user.

The sensor is preferably an RFID reader and the identification tag is an RFID tag.

Preferably there is provided data storage means to store data in relation to hand sanitizing by a plurality of individuals.

In another embodiment of the invention there is provided apparatus for drying hands in which the hand sanitizing means comprises at least one nozzle, connectable to supply of hand sanitizing substance, the nozzle being adapted to dispense hand sanitizing substance into the hand placement area. In this way, the hand sanitizing substance may be dispensed onto the user's hands while they use the device, resulting in clean, dry hands.

Preferably a ring of nozzles (now shown) may also be fitted at or near the entrance of the hand placement area resulting in the hands being sprayed with sanitizing fluid when the user is placing hands into the hand placement area.

In an alternative embodiment of the invention there is provided apparatus for drying hands in which the hand sanitizing means comprises a plurality of nozzles, at least partially surrounding the hand placement area. In this way, a thorough an even distribution of hand sanitizing substance may be achieved.

In a further embodiment of the invention there is provided apparatus for drying hands further comprising a HEPA filter in the airflow path. In this way, the device will reduce airborne micro-organisms in the circulating airflow.

In an alternative embodiment of the invention there is provided apparatus for drying hands further comprising a hand-washing basin. In this way, a single device may be installed that allows a user to wash, dry and sanitise their hands with the one device.

DETAILED DESCRIPTION OF THE INVENTION

The invention will now be more clearly understood from the following description of an embodiment thereof given by way of example only with reference to the accompanying drawings in which.

Figure 1:
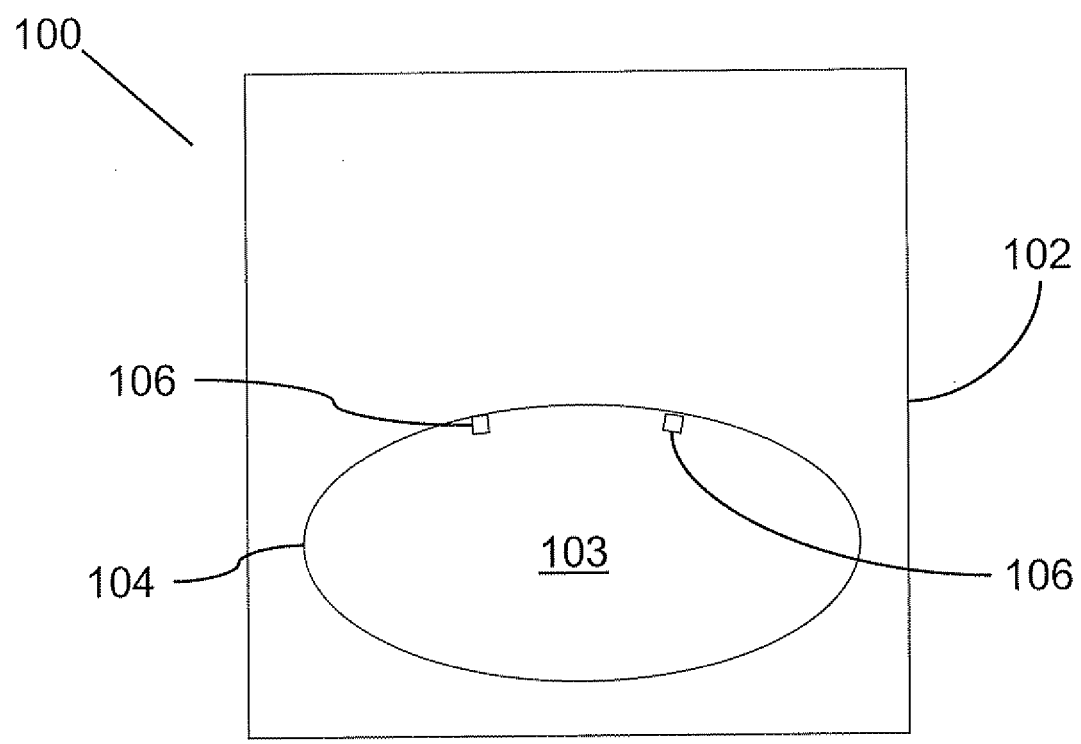
FIG. 1 is a front view of one embodiment according to the invention.

Referring to the drawings, and initially to FIG. 1 thereof, there is shown an apparatus for drying hands indicated generally by the reference numeral 100, comprising a housing or enclosure 102 having a hand placement area 103 defined in the lower half thereof by a substantially oval-shaped hand placement aperture 104 in the front cover part of the enclosure 102. The oval shape of the hand placement aperture 104 guides users to place their hands into the centre of the hand placement area 103. A plurality of nozzles 106 project into the hand placement area 103.

Figure 2:
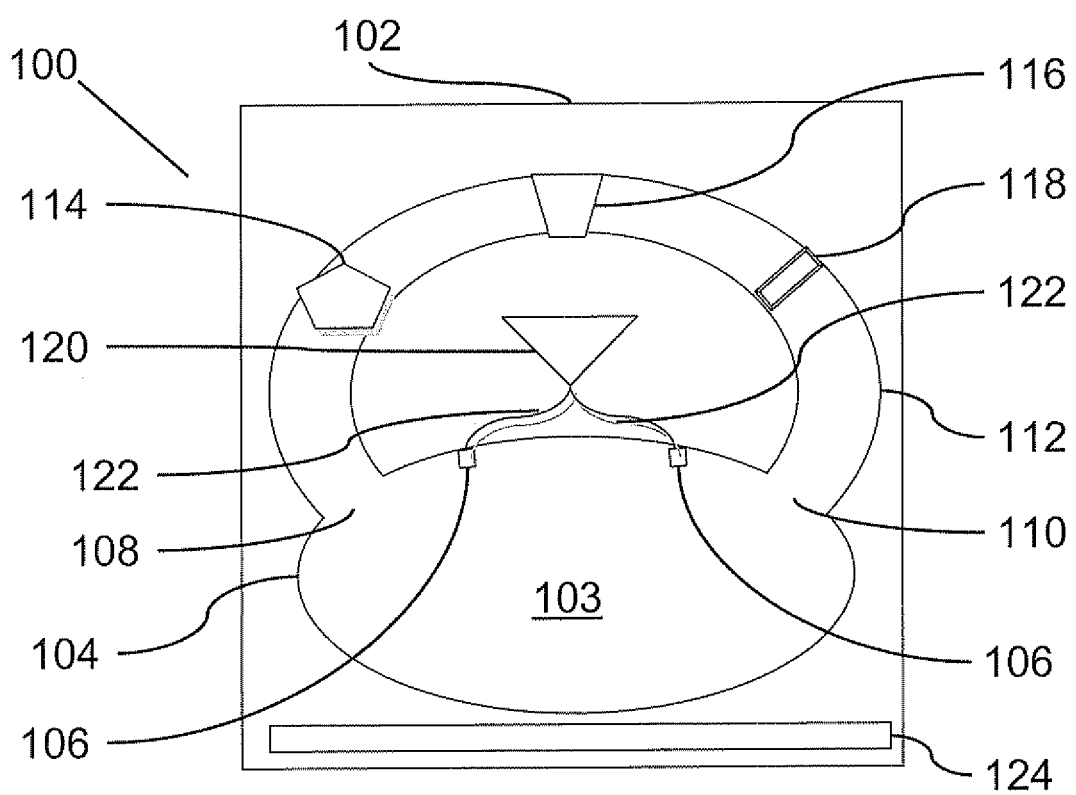
FIG. 2 is a front internal view of the embodiment of FIG. 1.

Referring now to FIG. 2, in which like parts have been given the same reference numerals as before, there is shown a view of the apparatus wherein the front cover of the enclosure 102 has been removed. It can be seen that the hand placement area 103 comprises an airflow inlet 108 and an airflow outlet 110, located in the top half of the hand placement area 103, in opposite quadrants. An airflow duct 112 is connected in a part-circular path between the airflow inlet 108 and the airflow outlet 110. An airflow generator 114 is located in the airflow duct 112. Together the airflow generator 114, airflow duct 112, airflow inlet 108 and airflow outlet 110 form means for generating a substantially circulating airflow, wherein part of that circulating airflow passes through the hand placement area 103.

Also optionally located in the airflow duct are a HEPA filter 116 to reduce the airborne micro-organisms in the circulating airflow and a heating element 118 to heat the air the exits the airflow duct 112 at the airflow outlet 110. The HEPA filter 116 and/or element 118 may not be included in the apparatus as desired.

The apparatus 100 further comprises a hand sanitizing means comprising a reservoir 120 for hand sanitizing substance, which reservoir 120 is connected to the plurality of nozzles 106 that extend into the hand placement area 103. The nozzles 106 are connected to the reservoir 120 by connecting hoses 122.

The apparatus comprises a fluid collection tray 124 in which excess hand sanitizing substance and fluid from a user's hand may be collected. In some cases, the fluid collection tray 124 will be connected to a drain outlet (not shown) for disposing of the fluid collected therein.

The apparatus further comprises activation means (not shown) which may comprise automatic activation mean which will detect the presence of a user's hand in the hand placement area 103 and thus activate the apparatus, or the activation mean may be a manual activation switch. Such automatic and manual activation means are well know and will not be described further here.

In use, the user either activates the manual activate means and places his hands in the hand placement area 103, or else simply places his hands in the hand placement area 103 and the automatic activation means causes the apparatus 100 to activate. Activation causes the hand sanitizing means to dispense a suitable amount of hand sanitizing substance into the hand placement area 103 and thus onto the hands of the user. Preferably, the hand sanitizing substance is sprayed into the hand placement area 103, from nozzles 106 for example in an aerosol formation, atomized, or other similar manner, thus providing substantially uniform distribution throughout the hand placement area.

The user then rubs the hand sanitizing substance over their hands for a period of time to ensure thorough distribution and effectiveness.

Next the airflow generator 114 activates, generating an airflow in the airflow duct 112. The airflow sucks in air at the airflow inlet 108 and blows out filtered, heated air at the airflow outlet 110. In this way an airflow through the hand placement area 103, from the airflow outlet 110 to the airflow inlet 108, is generated. This airflow both sucks and blows fluid from the user's hands while activated.

The quantity of hand sanitizing substance distributed will be determined by the dosage instructions from the manufacturer of the substance. Similarly, the time period between dispensing of the hand sanitizing substance and the initiation of the airflow will be set to allow sufficient time to the user to thoroughly rub the hand placement area over his hands. The manufacturer's instructions, if present, will be followed in this matter.

It will be understood by the person skilled in the art that the apparatus of the invention may be adapted for use with wet hands such that they are dried and then sanitized, or on dry hands that are simply sanitized and then dried.

Figure 3:
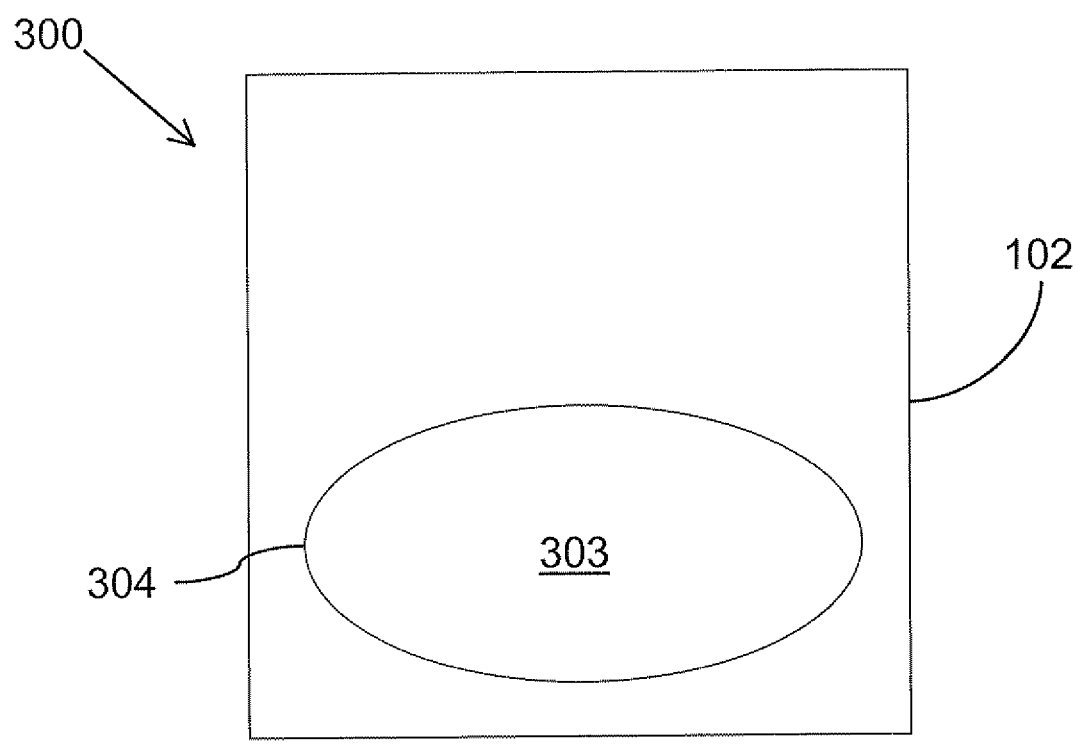
FIG. 3 is a front view of an alternative embodiment of the invention.

Referring now to FIG. 3, there is shown an alternative embodiment of apparatus for drying hands indicated generally by the reference numeral 300, comprising an substantially cuboid enclosure 302 having a hand placement area 303 defined in the lower half thereof by a substantially oval-shaped hand placement aperture 304 in the front cover part of the enclosure 302. The oval shape of the hand placement aperture 304 guides users to place their hands into the centre of the hand placement area 303.

The circulating airflow of the apparatus according to the invention reduces the distribution of micro-organisms by the drier as air is not blown out from the drier, but sucked into it. The air sucked into the apparatus is then filtered such that airborne micro-organisms are in fact removed from the air surrounding the apparatus instead of being spread therein.

Figure 4:
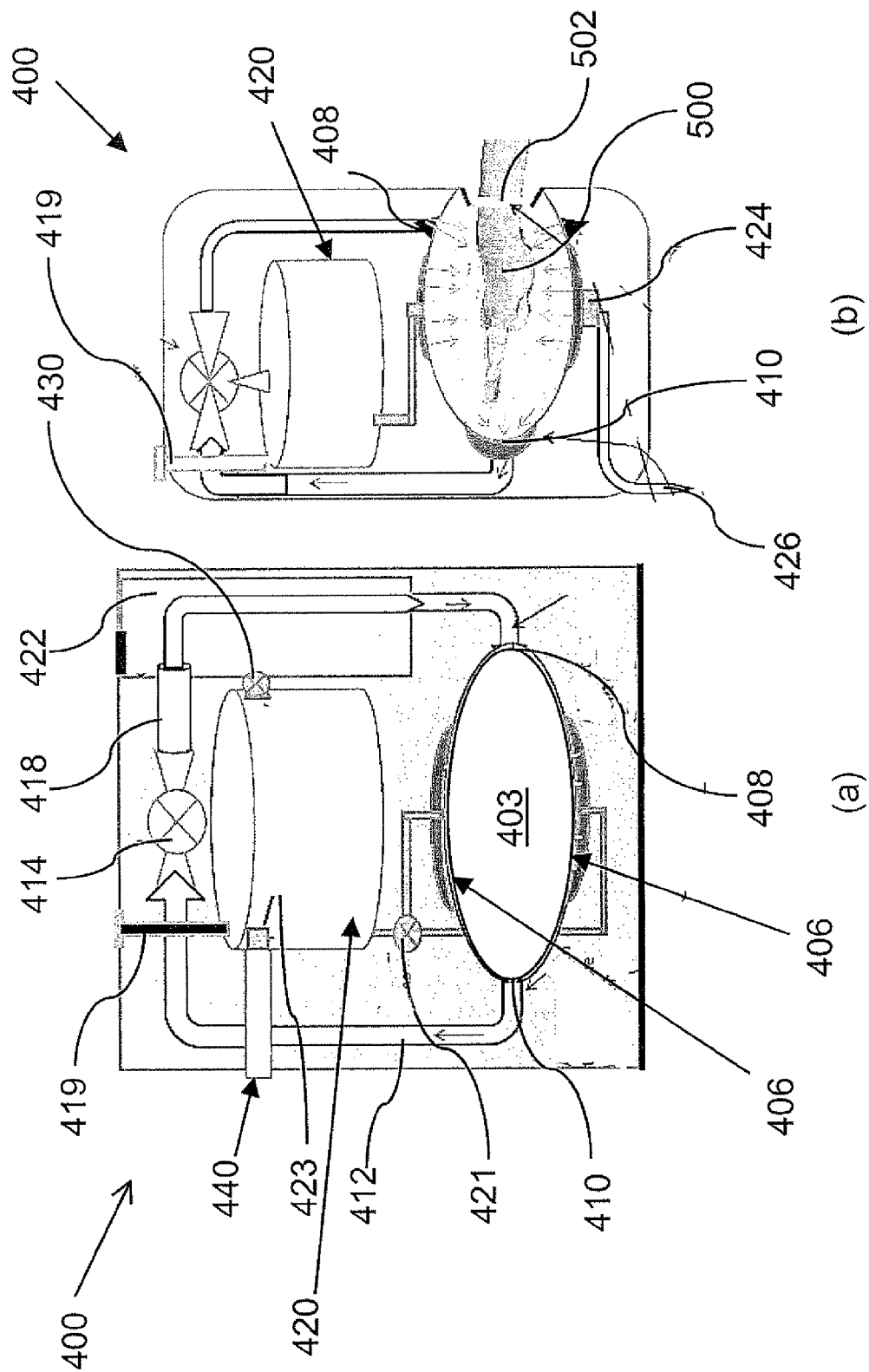
FIG. 4(a) is a front internal view of another embodiment of the invention.
FIG. 4(b) is a side internal view of the embodiment shown in FIG. 4(a)
Figure 5:
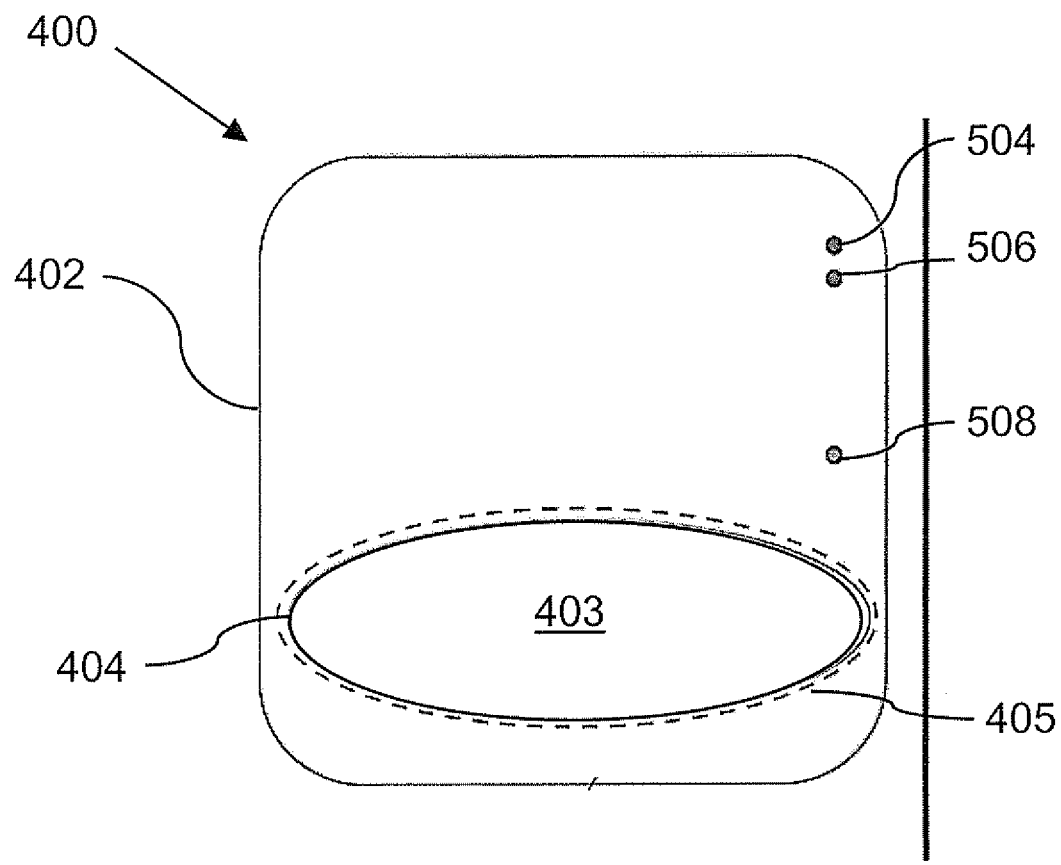
FIG. 5 is a front view of the embodiment shown in FIGS. 4(a) and (b).

Referring now to FIGS. 4(a) and (b) and FIG. 5, there is shown an alternative embodiment of apparatus for drying hands indicated generally by the reference numeral 400, comprising a substantially cuboid enclosure 402 having a hand placement area 403 defined in the lower half thereof by a substantially oval-shaped hand placement aperture 404 in the front cover part of the enclosure 402. The oval shape of the hand placement aperture 404 guides users to place their hands into the centre of the hand placement area 403. The hand placement aperture 404 is surrounded by an RFID reader 405.

It can be seen that the hand placement area 403 comprises an airflow inlet 408 and an airflow outlet 410, located at opposing sides of the hand placement area 403. The airflow inlet 408 is located towards the front of the hand placement area 403, while the airflow outlet 410 is located towards the rear of hand placement area 403. An airflow duct 412 is connected between the airflow inlet 408 and the airflow outlet 410. An airflow generator, in the form of a high-volume fan 414, is located in the airflow duct 412. Together the airflow generator 414, airflow duct 412, airflow inlet 408 and airflow outlet 410 form means for generating a substantially circulating airflow, wherein part of that circulating airflow passes through the hand placement area 403.

The airflow duct 412 may be fitted with a heating element 418 if desired, to heat the air in the substantially circulating airflow; and a filter 419 to remove contaminants from the airflow. The filter 419 is removable for cleaning and replacement.

The apparatus 400 further comprises a hand sanitizing means comprising a reservoir 420 for hand sanitizing fluid, which reservoir 420 is connected via an atomizer pump 421 to a plurality of nozzles 406 that are directed into the hand placement area 403. The reservoir 420 receives a supply of concentrated sanitizer liquid from a tank 422. The concentrated hand sanitizer is mixed with water from an external supply 440 that is fed to the reservoir 420, which water supply to the reservoir is controlled by a ball cock 423 or other valve means (not shown). The concentrated sanitizer liquid is supplied to the reservoir 420 by a dosing pump 430. The reservoir 420 comprises a sensor (not shown) that detects when the level of sanitizer fluid therein has dropped below a certain level. At that point, a command to refill the reservoir is triggered. The refilling action comprising two steps, the dosing pump 430 is activated to inject additional concentrated sanitizer liquid into the reservoir 420, and the reservoir is refilled with water. Typically the sanitizer solution will comprise 1 ml concentrated sanitizer to 50 ml water.

It will be appreciated that if a sensor (not shown) is used to activate the water supply to the reservoir, the purpose of the ball cock is to turn off the water supply when the level of liquid or solution in the reservoir 420 reaches a certain level. Further, it will be appreciated that where a suitable valve (not shown) is used to turn on and turn off the water supply the ball cock may be unnecessary.

The important aspect is that the dosing pump 430 and water supply 440 are suitably controlled by a sensor (not shown) to enable the solution in the reservoir 420 to be periodically topped up to a desired concentration level, of water/sanitizer liquid. The apparatus comprises a fluid collection tray 424 in which excess hand sanitizing substance and fluid from a user's hand may be collected. In some cases, the fluid collection tray 424 will be connected to a drain 426 for disposing of the fluid collected therein. The drain 426 may also be connected to the filter 419 for removal of any liquid that may be collected by the filter. This collection tray may also be fitted with an heating element to evaporate the excess fluid if no drain is available (ie corridor or hospital ward etc).

The apparatus 400 further comprises activation means (not shown) which may comprise automatic activation mean which will detect the presence of a user's hand in the hand placement area 403 and thus activate the apparatus, or the activation mean may be a manual activation switch. Possible activation means comprise a proximity sensors and/or infrared sensing means. Such automatic and manual activation means are well known and will not be described further here.

In FIG. 4(b), a user's hands 500 are shown in located in the hand placement area 403. The user is wearing an RFID wristband 502 which, in combination with the RFID reader 405 located around the hand placement area 403, operates to allow tracking of users who sanitise their hands with the apparatus. The RFID system may also operate to provide the activation means of the apparatus, i.e. to operate the atomiser pump and to start the fan 414, as appropriate.

The apparatus may therefore include data storage means (not shown) to store data, information and records in relation to hand sanitizing by a plurality of individuals. This may have particular applicability in the medical, food or other fields where hand hygiene is important.

In FIG. 5, the front of the enclosure is shown with a pair of warning lights, a concentrate low warning light 504 and a concentrate empty warning light 506. The enclosure further comprises an instruction light 508.

In use, the apparatus 400 is loaded with a supply of concentrated sanitizer into the tank 422 and the apparatus is connected to an external water supply typically by way of the plumbing in the building in which the apparatus 400 is installed. The concentrated sanitizer and water are mixed together in the reservoir 420, with the supply of water controlled by the ball cock 423, such that the reservoir contains a sanitizer solution suitable for dispensing onto a user's hands 500.

Next, when a user wishes to use the apparatus 400, he places his hands in the hand placement area 403 through the hand placement aperture 404. The activation means, either the RFID reader 405 in combination with RFID wristband 502 worn by the user, or other sensor means in or near the hand placement area 403, cause the atomiser pump to activate and dispense sanitizer solution through the nozzles 406 into the hand placement area 403. After the sanitizer solution has been dispensed, the airflow generator 414 is activated to generate a circulating airflow in the airflow duct such that the airflow passes through the hand placement area 403. As the airflow generator 414 is activated, the instruction light 508 comes on instruction the user to slowly remove their hands from the hand placement area 403, such that any excess fluid on their hands will be dried by the circulating airflow.

It will be understood by the person skilled in the art that the term airflow generator may refer to a fan and motor assembly, such as is known in the art. Preferably, the airflow generator will be capable of generating an airflow of 150 meters per second.

It will be understood that in some or all embodiments of the invention focussing on the sanitisation function thereof, the heating element in the apparatus will not be required, as the sanitisation substance will not require heat to evaporate.

It will be understood that the apparatus may comprise a plurality of nozzles, some positioned over the hand placement area and some there below, such that a user's hand, when placed in the hand placement area will be sprayed with hand sanitising substance from above and below to ensure a suitable distribution of the substance on the hands. Nozzles may also be located at the sides of the hand placement area, or anywhere else that would be suitable for dispensing the hand sanitising substance on the user's hands.

It will be understood that the invention may be used as a substitute for hand-washing in certain circumstances, and thus reducing the quantities of soap, water and energy required for cleaning of hands. The apparatus may also be equipped with a sink for situations where waterless sanitisation is insufficient, for example where the removal of solids or the like from the hands is required.

In the specification the terms 'comprise', 'comprises', 'comprised' and 'comprising' or any variation thereof and the terms 'include', 'includes', 'included' or 'including' or any variation thereof are considered to be totally interchangeable and they should all be afforded the widest possible interpretation.

The invention is not limited to the embodiment herein described, but may be varied in both construction and detail within the terms of the claims.

I claim:

1. An apparatus for drying and sanitizing hands, said apparatus comprising a housing having a hand placement area and a hand sanitizing means to spray a hand sanitizing fluid into the placement area, and an airflow generator to provide an airflow to dry hands in the placement area, said airflow generator being located between an inlet and an outlet for generating a circulating airflow, and wherein at least part of the circulating airflow passes through the hand placement area thereby providing a blowing force and a suction force in the hand placement area.

2. An apparatus as claimed in claim 1, further comprising a reservoir for hand sanitizing fluid.

3. An apparatus as claimed in claim 1, wherein the hand sanitizing means comprises at least one nozzle to direct a spray of hand sanitizing fluid into the placement area.

4. An apparatus as claimed in claim 3, wherein there is provided a plurality of nozzles.

5. An apparatus as claimed in claim 3, further comprising a reservoir for hand sanitizing fluid.

6. An apparatus as claimed in claim 5, wherein there is further provided a tank of concentrated sanitizer liquid connected to the reservoir for sanitizer fluid.

7. An apparatus as claimed in claim 6, wherein the reservoir for hand sanitizing fluid is connected to a water supply.

8. An apparatus as claimed in claim 7, wherein the water supply is controlled via a ball cock.

9. An apparatus as claimed in claim 7, wherein the tank is connected to the reservoir via a dosing pump.

10. An apparatus as claimed in claim 9, wherein the reservoir comprises a sensor means to control the water supply to the reservoir and to control the dosing pump to supply concentrated sanitizer liquid to the reservoir.

11. An apparatus as claimed in claim 10, wherein the dosing pump in use injects concentrate sanitizer liquid into the reservoir and water is supplied to the reservoir to achieve the preferred necessary concentration of sanitizer liquid.

12. An apparatus as claimed in claim 6, wherein there is provided an atomizer pump connected between the reservoir and the nozzle.

13. An apparatus as claimed in claim 5, wherein the reservoir for hand sanitizing fluid is connected to a water supply.

14. An apparatus as claimed in claim 5, wherein there is provided an atomizer pump connected between the reservoir and the nozzle.

15. An apparatus as claimed in claim 14, wherein there is provided a plurality of nozzles.

16. An apparatus as claimed in claim 1, wherein there is provided a sensor means to detect an identification tag on a user, to record usage of the apparatus by the user.

17. An apparatus as claimed in claim 16, wherein the sensor is an RFID reader and the identification tag is an RFID tag.

18. An apparatus as claimed in claim 16, wherein there is provided means to activate the apparatus, in response to detection of a tag worn by a user.

19. An apparatus as claimed in claim 18, wherein the sensor is an RFID reader and the identification tag is an RFID tag.

20. An apparatus as claimed in claim 16, wherein there is provided data storage means to store data in relation to hand sanitizing by a plurality of individuals.

21. An apparatus as claimed in claim 1, further comprising a HEPA filter in the airflow path for reducing airborne microorganisms in the circulating airflow.

22. An apparatus for sanitizing hands (400) comprising a housing (402) having a hand placement area (403) and a hand sanitizing means to spray a hand sanitizing fluid into the placement area (403), and means to provide an airflow to dry hands in the placement area, wherein the hand sanitizing means comprises at least one nozzle (406) to direct a spray of hand sanitizing fluid into the placement area, the apparatus further comprising a reservoir (420) for hand sanitizing fluid, wherein a tank (422) of concentrated sanitizer liquid is connected to the reservoir for sanitizer fluid, and wherein the reservoir for hand sanitizing fluid is connected to a water supply.

23. An apparatus for drying and sanitizing hands, said apparatus comprising a housing having a hand placement area and a hand sanitizing means to spray a hand sanitizing fluid into the placement area, and an airflow generator to provide an airflow to dry hands in the placement area, said airflow generator being located between an inlet and an outlet for generating a circulating airflow, wherein at least part of the circulating airflow passes through the hand placement area thereby providing a blowing force and a suction force in the hand placement area, the apparatus further comprising a reservoir (420) for hand sanitizing fluid, wherein a tank (422) of concentrated sanitizer liquid is connected to the reservoir for sanitizer fluid, and wherein the reservoir for hand sanitizing fluid is connected to a water supply.

* * * * *